US008241889B2

(12) United States Patent
Schisler et al.

(10) Patent No.: US 8,241,889 B2
(45) Date of Patent: Aug. 14, 2012

(54) **PROTHIOCONAZOLE TOLERANT *CRYPTOCOCCUS FLAVESCENS* STRAINS FOR BIOLOGICAL CONTROL OF FUSARIUM HEAD BLIGHT**

(75) Inventors: David A. Schisler, Morton, IL (US); Michael J. Boehm, Worthington, OH (US)

(73) Assignees: The United States of America as represented by the Secretary of State, Washington, DC (US); The Ohio State University Research Foundation, Columbus, OH (US)

( * ) Notice: Subject to any disclaimer, the term of this patent is extended or adjusted under 35 U.S.C. 154(b) by 413 days.

(21) Appl. No.: 12/511,275

(22) Filed: Jul. 29, 2009

(65) Prior Publication Data

US 2011/0027233 A1 Feb. 3, 2011

(51) Int. Cl.
*C12N 1/16* (2006.01)
*A01N 63/04* (2006.01)

(52) U.S. Cl. .................................. 435/255.3; 424/93.51

(58) Field of Classification Search ................ 435/252.3
See application file for complete search history.

*Primary Examiner* — Delia Ramirez

(74) *Attorney, Agent, or Firm* — John Fado; Randall E. Deck

(57) ABSTRACT

Strains of *Cryptococcus flavescens* which are superior antagonists of *F. graminearum* for suppression and control of FHB in cereals, particularly in wheat and barley, are described. The strains are prothioconazole tolerant variants of previously described *C. flavescens* OH 182.9 (NRRL Y-30216). Moreover, these prothioconazole tolerant variants exhibit significantly increased efficacy against *F. graminearum* in comparison to the parent strain OH 182.9.

17 Claims, No Drawings

PROTHIOCONAZOLE TOLERANT *CRYPTOCOCCUS FLAVESCENS* STRAINS FOR BIOLOGICAL CONTROL OF FUSARIUM HEAD BLIGHT

BACKGROUND OF THE INVENTION

1. Field of the Invention

The invention is drawn to novel biocontrol agents for control of *Fusarium* head blight.

2. Description of the Prior Art

*Fusarium* head blight (FHB) is a devastating disease of wheat and barley throughout the semi-humid and humid cereal producing regions of the world (McMullen et al., 1997, Scab of wheat and barley: are emerging disease of devastating impact. Plant Disease, 81, 1340-1348; Muthomi et al., 2002, Susceptibility of Kenyan wheat varieties to head blight, fungal invasion and deoxynivalenol accumulation inoculated with *Fusarium graminearum*, Journal of Phytopathology, 150, 30-36; Yu. Gagkaeva and Yli-Mattila, 2004, Genetic diversity of *Fusarium graminearum* in Europe and Asia, European Journal of Plant Pathology, 110, 551-562). FHB is caused primarily by *Fusarium graminearum* Schwabe Group 2 (Aoki and O'Donnell, 1999, Morphological and molecular characterization of *Fusarium pseudograminearum* sp. nov., formerly recognized as the Group 1 population of *F. graminearum*, Mycologia, 91, 597-609) [perfect state=*Gibberella zeae* (Schwein.) Fetch]. In addition to causing grain yield loss, *G. zeae* can produce mycotoxins such as the estrogenic toxin zearalenone (F-2) (Hesseltine et al., 1978, Fungi, especially *Gibberella zeae*, and zearalenone occurrence in wheat. Mycologia, 70, 14-18) and the trichothecene deoxynivalenol (DON, vomitoxin) (Snijders, 1990, *Fusarium* head blight and mycotoxin contamination of wheat, a review. Netherlands Journal of Plant Pathology, 96, 187-198) that can have a deleterious effect on grain quality [Cardwell et al., 2001, Mycotoxins: the cost of achieving food security and food quality, APS Net: Feature story August, 2001] and animal health [Marasas, 1991, Toxigenic Fusaria, in: Mycotoxins and Animal Foods, J. E. Smith and R. S. Henderson, eds., CRC Press, Inc., Boca Raton, Fla.; Beardall and Miller, 1994, Diseases in humans with mycotoxins as possible causes, in Mycotoxins in Grain: Compounds Other than Aflatoxin (MILLER, J. D. & TRENHOLM, H. L., Eds.). Eagan Press, St. Paul, Minn., pp. 387-39; Pestka and Bondy, 1994, Immunotoxic effects of mycotoxins, in Mycotoxins in Grain: Compounds Other than Aflatoxin (MILLER, J. D. & TRENHOLM, H. L., Eds.) Eagan Press, St. Paul, Minn., pp. 339-358].

Reducing the impact of FHB on grain production and quality remains an intractable problem. Fungicides sometimes have reduced FHB [Wilcoxson, 1996, Fungicides for control of *Fusarium* head blight, Int. J. Tropical Plant Disease, 14, 27-50; Suty and Mauler-Machnik, 1997, *Fusarium* ear blight on wheat-epidemiology and control of *Gibberella zeae*, the teleomorph of *Fusarium graminearum* with Folicur, in Diagnosis and Identification of Plant Pathogens, Proceedings of the 4th International Symposium of the European Foundation for Plant Pathology (DEHNE, H. W., ADAM, G., DIEKMANN, M., FRAHM, J., MAULER-MACHNIK & VAN HALTEREN, P., Eds). Kluwer Academic Publishers, Dordrecht., pp. 243-246; Jones, 1999, Seedling blight development and control in spring wheat damaged by *Fusarium graminearum* Group 2. Plant Disease, 83, 1013-1018], but residues, reports of fungicide resistance and instances of DON content increases in grain can be concerns with their use [Mauler-Machnik and Zahn, 1994, Ear fusarioses in wheat-new findings on their epidemiology and control with Folicur (tebuconazole). Pflanzenschutz-Nachrichten Bayer, 47, 129-155; Ramirez et al., 2004, Impact of environmental factors and fungicides on growth and deoxynivalenol production by *Fusarium graminearum* isolates from Argentinian wheat. Crop Protection, 23, 117-125; Chen et al, 2000, Recent advances in wheat head scab research in China, in Proc. Int. Symp. Wheat Improvement for Scab Resistance (RAUPP, W. J., MA, Z., CHEN, P. & LIU, D., Eds.). Nanjing Agricultural University, Jiangsu, China, pp. 258-273; Gale et al, 2002, Population analysis of *Fusarium graminearum* from wheat fields in eastern China, Phytopathology, 92, 1315-1322]. Although the development of resistant cultivars or anatomically altered varieties (Legzdina and Buerstmayr, 2004, Comparison of infection with *Fusarium* head blight and accumulation of mycotoxins in grain of hulless and covered barley, Journal of Cereal Science, 40, 61-67) of small grains holds promise in reducing FHB, highly resistant cultivars with ideal agronomic traits have not been developed (Johnston, 1994; Bushnell et al., 1998, Genetic engineering of disease resistance in cereals, Canadian Journal of Plant Pathology, 20, 137-149; Bai et al., 2000, Inheritance of resistance to *Fusarium graminearum* in wheat, Theoretical and Applied Genetics, 100, 1-8). The genetic diversity of *G. zeae* [O'Donnell et al., 2004, Genealogical concordance between the mating type locus and seven other nuclear genes supports formal recognition of nine phylogenetically distinct species within the *Fusarium graminearium* Glade, Fungal Genetics and Biology, 41, 600-623; McCallum et al., 2004, Barrage zone formation between vegetatively incompatible *Fusarium graminearum* (*Gibberella zeae*) isolates. Phytopathology, 94, 432-437; Walker et al., 2001, Variation among isolates of *Fusarium graminearum* associated with *Fusarium* head blight in North Carolina, Plant Disease, 85, 404-410; Cumagun et al., 2004, Genetic mapping of pathogenicity and aggressiveness of *Gibberella zeae* (*Fusarium graminearum*) toward wheat, Phytopathology, 94, 520-526] raises concerns regarding how durable the efficacy of fungicides and resistant cultivars will be. Conventional tillage of fields is partially effective in reducing pathogen inoculum production and, concomitantly, FHB (Miller et al., 1998, Effect of tillage practice on *Fusarium* head blight of wheat, Canadian Journal of Plant Pathology, 20, 95-103; Dill-Macky and Jones, 2000, The effect of previous crop residues and tillage on *Fusarium* head blight of wheat, Plant Disease, 84, 71-76; Pereyra et al., 2004, Survival and inoculum production of *Gibberella zeae* in wheat residue, Plant Disease, 88, 724-730), but minimum tillage is the preferred agricultural practice for soil conservation. Considering the potential of long distance inoculum dispersal and the diverse crops that can act as alternative hosts of the pathogen (Chongo et al., 2001, Reaction of seedling roots of 14 crop species to *Fusarium graminearum* from wheat head, Canadian Journal of Plant Pathology, 23, 132-137), crop rotation is an untenable solution.

Biological control of FHB has attracted considerable interest since the mid 1990's, and significant advances have been achieved [Perondi et al., 1996, Controle microbiologico da giberela do trigo, Fitopatologia Brasiliera, 21, 243-249; Bujold et al., 2001, Effect of Microsphaeropsis sp. on the production of perithecia and ascospores of *Gibbereila zeae*, Plant Disease, 85, 977-984; Schisler et al., 2002, Biological control of *Fusarium* head blight of wheat and deoxynivalenol levels in grain via use of microbial antagonists, in Mycotoxins and Food Safety (DeVRIES, J. W., TRUCKSESS, M. W. & JACKSON, L. S., Eds.). Kluwer Academic/Plenum Publishers, New York, pp. 53-69; da Luz et al, 2003, Biological control of *Fusarium graminearum*, in *Fusarium* head blight of wheat and barley (LEONARD, K. J. & BUSHNELL, W. R., Eds.) APS Press, St. Paul, Minn., 381-394; Gilbert & Fernando. 2004, Epidemiology and biological control of *Gibberella zeae* (anamorph *Fusarium graminearum*). Canadian Journal of Plant Pathology, 26, 1-9]. Public acceptance, compatibility with other disease management measures, and durability are all favorable factors in support of developing strategies for biologically controlling FHB.

Schisler et al. (U.S. Pat. No. 6,562,337) described the isolation of four yeast and one bacterium which were superior antagonists capable of suppressing FHB. These microorganisms, which were obtained from the anthers of wheat, included the yeast *Cryptococcus flavescens* OH 182.9 (originally classified as *C. nodaensis*) which was deposited in the Agricultural Research Service Culture Collection (NRRL) under deposit accession no. NRRL Y-30216. Recently, Schisler et al. (2006, Selection and evaluation of the potential of choline-metabolizing microbial strains to reduce *Fusarium* head blight, Biological Control, 39, 497-506) disclosed selecting choline-utilizing strains of microorganisms as biological control agents against FHB.

Although efforts for developing biological control agents for FHB have been effective, the development and use of chemical fungicides remain a valuable tool in the arsenal of agents for the reduction of FHB in cereals. Most recently the fungicidal chemical prothioconazole has received an exemption status for use on wheat at flowering for the reduction of FHB.

However, despite these and other advances, the need remains for improved microorganisms for use in the biological control of FHB.

SUMMARY OF THE INVENTION

We have now discovered novel strains of *Cryptococcus flavescens* which are superior antagonists of *F. graminearum*. These microorganisms are effective for suppression and control of FHB in cereals, particularly in wheat and barley. The strains of the invention are prothioconazole tolerant variants of previously described *C. flavescens* OH 182.9 (NRRL Y-30216). Moreover, these prothioconazole tolerant variants surprisingly exhibit significantly increased efficacy against *F. graminearum* in comparison to the parent strain OH 182.9.

In accordance with this discovery, it is an object of this invention to provide novel microbial strains that suppress the profusion of *F. graminearum* in heads of wheat and barley.

Another object of this invention is to provide novel microbial strains which are effective for the suppression of *F. graminearum* in heads of wheat and barley, and which are also tolerant to the fungicide prothioconazole.

A further object of this invention is to provide novel microbial strains which are effective for the control of *F. graminearum* in heads of wheat and barley which can be applied in concert with the fungicide prothioconazole and its derivatives.

This and other objects of the invention will become readily apparent from the ensuing description.

DEPOSIT OF BIOLOGICAL MATERIAL

Two prothioconazole tolerant strains of *Cryptococcus flavescens*, OH 182.9 variant 3C and OH 182.9 variant 4C, have been deposited on May 21, 2010 under the provisions of the Budapest Treaty in the Agricultural Research Service Culture Collection (NRRL), 1815 N. University St., Peoria, Ili, 61604, USA, and have been assigned Deposit Accession Nos. NRRL Y-50378 and NRRL Y-50379, respectively. The strains are yeasts which exhibit morphological and cultural properties characteristic of *Cryptococcus flavescens*, and their identity has been confirmed by sequence analysis of the D1/D2 domains of the 26S rRNA gene and the ITS 1+2 regions of the rRNA gene using standard methods (Okoli et al., 2006, *Cryptotrichosporon anacardii* gen. nov., sp. nov., a new trichosporonoid capsulate basidiomycetous yeast from Nigeria that is able to form melanin on niger seed agar. FEMS Yeast Res, 7:339-350). The phylogenetic tree was constructed using neighbor joining with the uncorrected ('p') substitution model, alignment gaps were treated as missing characters, and all characters were unordered and of equal weight. Bootstrap values were based on 100 replicates.

DETAILED DESCRIPTION OF THE INVENTION

For purposes of this invention it is understood that the use of term *Fusarium* is intended to include both the sexual (teleomorphic) stage of this organism and also the asexual (anamorphic) stage, also referred to as the perfect and imperfect fungal stages, respectively. For example, the anamorphic stage of *Gibberella zeae* is known as *Fusarium graminearum*, the causative agent of FHB. This disease results when the flower or head (also known as seed head) becomes inoculated with conidia produced by the imperfect form OR ascospores produced by the perfect form of this fungus with infection of the inoculated head ensuing after the inoculation event.

The expression "superior antagonist" used herein in reference to a microorganism is intended to mean that the subject strain exhibits a degree of inhibition of *Fusarium*-induced head blight exceeding, at a statistically significant level, that of an untreated control.

The term cereal as used herein is intended to refer to any cereal species that is normally susceptible to FHB. Cereals reported to be susceptible include wheat, barley, oats, and triticale, though wheat and barley are the two crops in which this disease presents a significant economic problem. Any of these cereals may be target species for FHB control.

*F. graminearum* primarily infects the heads (flower heads, seed heads, or spikes) of cereal plants from the time of flowering through the soft dough stage of head development. Germinated conidia or ascospores of *F. graminearum* penetrate through anthers and associated tissues to initiate infection of the host and the development of symptoms of FHB.

The *F. graminearum* antagonists of this invention are variant strains derived from *Cryptococcus flavescens* OH 182.9 (NRRL Y-30216, formerly identified as *C. nodaensis*) which was previously described in U.S. Pat. No. 6,562,337, the contents of which are incorporated by reference herein. Although *C. flavescens* OH 182.9 is effective in reducing FHB in cereals, unfortunately it is sensitive even to low concentrations of the fungicide prothioconazole. This sensitivity has limited the application of the *C. flavescens* against FHB in fields which are or will also be treated with prothioconazole. We have now discovered that variants or mutants of *C. flavescens*OH 182.9 which exhibit significantly greater tolerance to prothioconazole (capable of growth in the presence of prothioconazole) than the parent OH 182.9 may be produced. Moreover, we have surprisingly discovered that at least some of the prothioconazole tolerant strains are superior antagonists to *F. graminearum*, and exhibit significantly greater efficacy against FHB than the parent *C. flavescens* OH 182.9.

The prothioconazole tolerant strains of the invention are produced using a protracted series of culturing events where the yeast is exposed to increasing concentrations of prothioconazole. As described in greater detail in the Example, the parent *C. flavescens* OH 182.9 is cultivated in a nutrient medium containing between at least a trace concentration up to about 4 ppm prothioconazole, preferably about 1 ppm prothioconazole, and strains exhibiting growth are selected for culture at higher concentrations of prothioconazole. The process is repeated with the selected strains cultivated at gradually increasing concentrations of the fungicide to ultimately select strains capable of growth in nutrient media containing between at least about 2 ppm up to about 10 ppm prothioconazole, preferably about 5 ppm prothioconazole.

Recovered prothioconazole tolerant *C. flavescens* strains are subsequently examined for efficacy in reducing the severity of FHB in a desired cereal plant, preferably wheat. In brief, the prothioconazole tolerant variants are passed through a plant bioassay in which cells of the yeasts are introduced to a cereal plant seed head inoculated with conidia of *F. graminearum*. In one preferred embodiment, the *F. graminearum* will be produced on a solidified growth medium and the level of harvested inoculum should be on the order of about $10^4$-$10^6$ conidia/ml, preferably about $10^5$ conidia/ml of aqueous suspension. The cells of prothioconazole tolerant yeast antagonist in medium or a suitable buffer are introduced at a level of approximately $10^7$-$10^8$ cfu/ml. In one embodiment of the invention, the conidia of *F. graminearum* and cells of the test strain are combined in a weak phosphate buffer and approximately 10 μL of the suspension are used to inoculate the plant seed head. The plants are then cultivated under conditions of near 100% relative humidity conducive to infection by the fungus for a period of about 3 days. After a period of time sufficient for noticeable development of the disease (usually at least about 2 weeks post inoculation), yeast variants used to treat seed heads and that reduce visible symptoms of FHB are selected for subsequent evaluation.

Prothioconazole tolerant yeast variants selected in the plant bioassay described above are optionally subjected to a second, more highly replicated plant seed head bioassay similar to the first. The yeast are again grown on a suitable medium until sufficiently expanded for use in the bioassay. However, in this second plant bioassay, it is preferable to grow the strains in liquid culture since this practice is widely used in industry and, antagonists must show bioefficacy when grown under liquid culture conditions. Colonized broth containing cells of individual strains and a conidial suspension of *F. graminearum* are used to inoculate seed heads as previously described. The cells and conidial suspension may be precombined prior to inoculation. As in the first plant bioassay, yeast variants used to treat seed heads and that reduce visible symptoms of FHB are selected as candidate antagonists.

Confirmation of antagonist efficacy in controlling *F. graminearum* can be made in scaled-up greenhouse studies or in field studies in which flowering plants are treated with cells of the test strains, before, during, or after inoculation with conidia of *F. graminearum*. The plant treatment can be conducted in the same manner as a bona fide field application.

Prothioconazole tolerant variants of OH 182.9 are determined to be superior to the wild type OH 182.9 progenitor strain if, when progenitor and variant line cells are produced using comparable liquid culture growth techniques, the prothioconazole tolerant variants reduce disease severity symptoms by at least 50% or at least 25% more than the progenitor strain in replicated greenhouse or field trials on wheat, respectively. Disease severity is determined by calculating the average percentage of the surface area of individual wheat heads that exhibit symptoms of infection by *F. graminearum*.

Using the aforementioned method we have isolated two novel prothioconazole tolerant strains of superior FHB antagonist: *Cryptococcus flavescens*, OH 182.9 variant 3C and OH 182.9 variant 4C. It is envisioned that the method may be repeated to isolate additional prothioconazole tolerant variants of *C. flavescens* OH 182.9 which exhibit significantly greater efficacy in reducing FHB in cereal plants.

The prothioconazole tolerant variants of *C. flavescens* OH 182.9 will typically be grown in aerobic liquid cultures on media which contain sources of carbon, nitrogen, and inorganic salts assimilable by the microorganism and supportive of efficient cell growth. Preferred carbon sources are hexoses such as glucose, but other assimilable sources such as amino acids, may be substituted. Many inorganic and proteinaceous materials may be used as nitrogen sources in the growth process. Preferred nitrogen sources are amino acids and urea but others include gaseous ammonia, inorganic salts of nitrate and ammonium, vitamins, purines, pyrimidines, yeast extract, beef extract, proteose peptone, soybean meal, hydrolysates of casein, distiller's solubles, and the like. Among the inorganic minerals that can be incorporated into the nutrient medium are the customary salts capable of yielding calcium, zinc, iron, manganese, magnesium, copper, cobalt, potassium, sodium, molybdate, phosphate, sulfate, chloride, borate, and like ions.

For the yeast of the invention, cell growth can be achieved at temperatures between 1 and 36° C., with the preferred temperature being in the range of 15-30° C. The pH of the nutrient medium can vary between 4 and 9, but the preferred operating range is pH 6-8. Ordinarily, maximal cell yield is obtained in 20-72 hours after inoculation.

As described in greater detail hereinbelow, control of FHB may be effected by application of one or more of the prothioconazole tolerant variants of *C. flavescens* OH 182.9 to the head (also referred to as seed head) of a cereal plant. As used herein, the "head" or "seed head" refers to the spike that contains seeds or the progenitors of seeds. The antagonists are applied in an amount effective to reduce the level of FHB relative to that in an untreated control.

Although the above-mentioned prothioconazole tolerant variants are effective when used alone, in an optional yet preferred embodiment, they are applied in combination with other known chemical or biological control agents for FHB. As noted above, owing to their tolerance to prothioconazole, the variants may be applied in combination with prothioconazole or its derivatives. Alternatively, the variants may be applied to cereal plants which have been or will be treated separately with prothioconazole or its derivatives. A variety of other biological control agents are suitable for use herein and include but are not limited to those disclosed by Perondi et al., 1996, ibid; Bujold et al., 2001, ibid; Schisler et al., 2002, ibid; da Luz et al., 2003, ibid; Gilbert & Fernando, 2004, ibid; and Schisler et al., U.S. Pat. Nos. 6,562,337 and 6,312,940, and U.S. application Ser. No. 11/640,091, filed Dec. 15, 2006; the contents of all of which are incorporated by reference herein. Use in combination with the microbial antagonists disclosed in the Schisler U.S. patents and pending application is preferred, specifically *Bacillus* sp. (NRRL B-30210), *Bacillus* sp. (NRRL B-30211), *Torula aurea* (recently renamed *Cryptococcus aureus*)(NRRL Y-30213), an unidentified yeast (NRRL Y-30214), *Bacillus* sp. (NRRL B-30212), and *Torula* sp. (recently renamed *Cryptococcus aureus*)(NRRL Y-30215). These additional antagonists may be applied with the antagonists of the invention, such as in a mixture, or they may be applied separately or at different times.

The prothioconazole tolerant variants of the invention can be applied by any conventional method to the surfaces of cereal heads. For example, they can be applied as an aqueous spray, as a wettable powder, or as a dust. Formulations designed for these modes of application will usually include a suitable liquid or solid carrier together with other adjuvants, such as wetting agents, sticking agents and the like. Starch, polysaccharides, sodium alginate, cellulose, etc. are, often used in such formulations as carriers and sticking agents.

The expressions "an effective amount" and "a suppressive amount" are used herein in reference to that quantity of antagonist treatment which is necessary to obtain a reduction in the level of disease relative to that occurring in an untreated control under suitable conditions of treatment as described herein. The actual rate of application of a liquid formulation will usually vary from a minimum of about $1\times10^3$ to about $1\times10^{10}$ viable cells/ml and preferably from about $1\times10^6$ to about $5\times10^9$ viable cells/ml. Under most conditions, the strains of the invention described in the example, below, would be optimally effective at application rates in the range of about $1\times10^6$ to $1\times10^9$ viable cells/ml, assuming a mode of application which would achieve substantially uniform contact of at least about 50% of the wheat head. If the antagonists are applied as a solid formulation, the rate of application should be controlled to result in a comparable number of viable cells per unit area of cereal head surface as obtained by the aforementioned rates of liquid treatment.

It is envisioned that the temperatures at which the antagonists are effective would range from about 5° C. to about 35° C. The preferred temperature range is 15-30° C., and the optimal range is considered to be 18-28° C.

The antagonists can theoretically be applied to the seed head at any time after the boot stage and before the hard dough stage of cereal development. The cereal head is only susceptible to infection by *F. graminearum* from the onset of flowering (anthesis) through the soft dough stage of kernel development. Thus, the best time to apply the biological control agents would be from the time immediately preceding flowering until as late as the soft dough stage of kernel development. Application of antagonists to heads before flowering would allow antagonists to have colonized wheat head parts prior to the wheat head becoming susceptible to infection. Additionally, antagonists would be well positioned to colonize and protect anthers as they emerge from florets. However, it is expected that the antagonists would still be effective if applied after flowering has begun, but before the hard dough stage of development. However, it is anticipated that long delays may decrease the effectiveness of the treatment depending on methods of cell formulation and application.

The following example is intended only to further illustrate the invention and are not intended to limit the scope of the invention which is defined by the claims.

Example 1

In order to produce prothioconazole tolerant variants of *Fusarium* head blight antagonist *Cryptococcus flavescens* OH 182.9 (NRRL Y-30216), pure cultures of the strain were initiated on ⅕ strength Tryptic soy broth agar (TSBA) from 10% glycerol stocks of the strain stored at −80° C. After 24 hours growth at 25° C., cells were transferred to 10 ml of ⅕ strength Tryptic soy broth (TSB) containing 1 ppm of the fungicide prothioconazole (PTC) in 50 ml Erlenmeyer flasks to obtain an initial optical density (A620) of approximately 0.100. Flasks were shaken at 250 rpm and plated after 5 days incubation at 25° C. onto ⅕ TSBA+1 ppm PTC. After incubating at 25° C. for several days, plates contained several colonies that had obtained a larger size than the majority of colonies produced on the ⅕ TSBA+1 ppm PTC medium. Four of these colonies were selected and streaked for purity on ⅕ TSBA+1 ppm PTC. The process of liquid culture growth of these 4 putative PTC tolerant variants was then repeated 4-5 times with the concentration of PTC in the liquid and solid media being gradually increased to a final concentration of 5 ppm and the largest colony produced by each of the 4 separate variant lines being chosen to start the next cycle of growth in liquid culture containing a slightly higher concentration of PTC.

Each of the 4 variant lines were then evaluated for equivalence to the wild type progenitor strain of OH 182.9 based on efficacy in reducing *Fusarium* head blight of wheat in greenhouse tests as follows. Hard red spring wheat (cultivar Norm) was grown in plant growth chambers prior to conducting plant bioassays on greenhouse benches. Biomass of progenitor strain OH 182.9 and PTCT variants 1C, 3C, 4C and 5C was produced in non-baffled, 125 ml Erlenmeyer flasks containing 25 ml of liquid medium (SDCL, Slininger et al. 2003. Postharvest biological control of potato sprouting by *Fusarium* dry rot suppressive bacteria. Biocontrol Science and Technology. 13:477-494) that was incubated at 250 rpm, 2.5 cm orbit and 25° C. for 72 h and diluted to ¼ strength with $dH_2O$ before use. Conidial inoculum of the FHB pathogen *Gibberella zeae* strain Z-3639 was produced on clarified V8 juice agar under 12 h/day fluorescent light for 7 days at 24° C. At wheat anthesis, cells of OH 182.9 were misted onto approximately 14 wheat heads per treatment followed immediately by a mist application of a conidial suspension ($3\times10^4$ conidia/ml). Heads treated with water followed by the conidial suspension served as "pathogen only" controls. Plants were placed in humidity tents for 3 days, scored for disease severity after 16 days and log growth rate in ⅕ TSB not containing PTC. Disease severity was determined by calculating the average percentage of the surface area of individual wheat heads that exhibit symptoms of infection by *F. graminearum*. The variant lines were also compared for total colony forming units per ml (cfu/ml) achieved when grown in ⅕ TSB+5 ppm PTC medium. The progenitor strain of OH 182.9 does not grow in this medium while all PTC tolerant variants of OH 182.9 produced in excess of $5\times10^7$ CFU/ml.

Prothioconazole tolerant variants of *C. flavescens* OH 182.9 3C and 4C exhibited significantly greater efficacy than the OH 182.9 parent and were retained. The results are shown in Tables 1-3.

It is understood that the foregoing detailed description is given merely by way of illustration and that modifications and variations may be made therein without departing from the spirit and scope of the invention.

TABLE 1

Influence of yeast antagonist OH 182.9, prothioconazole tolerant variant 4C of OH 182.9, prothioconazole and combinations thereof on *Fusarium* head blight in greenhouse trials[a, b]

| | Wheat Cultivar Norm | | | | | |
|---|---|---|---|---|---|---|
| Treatment[c] | DS (%) | Change vs Control (%) | DI (%) | Change vs Control (%) | 100 Kwt (g) | Change vs Control % |
| Untreated control | $42^A$ | 0 | $54^A$ | 0 | $3.0^B$ | 0 |
| OH 182.9 Wild Type | $27^{AB}$ | −36 | $38^{AB}$ | −30 | $3.6^A$ | 20 |
| OH 182.9 Variant 4C | $7^{CD}$ | −83 | $16^{BC}$ | −70 | $4.1^A$ | 37 |
| OH 182.9 WT + Proline | $1^D$ | −98 | $8^C$ | −85 | $4.3^A$ | 37 |
| OH 182.9 4C + | $0^D$ | −100 | $0^C$ | −100 | $4.1^A$ | 37 |

TABLE 1-continued

Influence of yeast antagonist OH 182.9, prothioconazole tolerant variant 4C of OH 182.9, prothioconazole and combinations thereof on *Fusarium* head blight in greenhouse trials[a, b]

| | Wheat Cultivar Norm | | | | | |
|---|---|---|---|---|---|---|
| Treatment[c] | DS (%) | Change vs Control (%) | DI (%) | Change vs Control (%) | 100 Kwt (g) | Change vs Control % |
| Proline | | | | | | |
| Proline Only | $0^{D}$ | −100 | $0^{C}$ | −100 | $4.0^{A}$ | 33 |
| P value | 0.001 | | 0.001 | | 0.001 | |

[a]Within a column, means not followed by the same letter are significantly different (P · 0.05, Bonferroni mean separation)
[b]DS = Disease severity, DI = Disease incidence, 100 Kwt = One hundred kernel weight
[c]Proline = Commercial formulation of prothioconazole applied at a rate equivalent to 5 oz/acre, OH 182.9 WT = Wild type strain of OH 182.9

TABLE 2

2008 field trial results at Peoria, IL: Influence of prothioconazole, yeast antagonist OH 182.9, prothioconazole tolerant variants 3C and 4C of OH 182.9, and combinations thereof on FHB disease parameters on winter wheat cultivar Pioneer Brand 2545[a, b]

| | Wheat Cultivar Pioneer Brand 2545 | | | |
|---|---|---|---|---|
| Treatment[c] | DS (%) | DI (%) | 100 KWT (g) | DON (ppm) |
| Untreated control | $8.0^{A}$ | $41.3^{A}$ | $3.07^{DE}$ | $11.8^{A}$ |
| Proline (5 oz/acre) | $1.5^{DEF}$ | $8.0^{F}$ | $3.57^{AB}$ | $3.9^{BC}$ |
| OH 182.9 WT | $7.6^{AB}$ | $31.2^{ABC}$ | $2.99^{E}$ | $13.6^{A}$ |
| OH 182.9 variant 3C | $5.3^{ABC}$ | $29.6^{BCD}$ | $3.26^{BCDE}$ | $10.4^{AB}$ |
| OH 182.9 variant 4C | $4.6^{BCD}$ | $24.5^{CD}$ | $3.13^{CDE}$ | $7.0^{ABC}$ |
| OH 182.9 3C + Proline | $1.4^{DEF}$ | $8.8^{F}$ | $3.49^{ABC}$ | $2.3^{C}$ |
| OH 182.9 4C + Proline | $1.6^{DEF}$ | $10.7^{EF}$ | $3.47^{ABC}$ | $2.4^{C}$ |
| Proline + WT (24 h delay) | $2.3^{CDEF}$ | $10.9^{EF}$ | $3.64^{A}$ | $2.6^{C}$ |
| Proline + 3C (24 h delay) | $0.6^{F}$ | $4.5^{F}$ | $3.43^{ABCD}$ | $1.1^{C}$ |
| P value | 0.001 | 0.001 | 0.001 | 0.001 |

[a]Within a column, means followed not followed by the same letter are significantly different (P < 0.05 Bonferroni mean separation)
[b]DS = Disease severity, DI = Disease incidence, 100 KWT = One hundred kernel weight, DON = Deoxynivalenol
[c]Proline = Commercial formulation of prothioconazole applied at a rate equivalent to 5 oz/acre, OH 182.9 WT = Wild type strain of OH 182.9

TABLE 3

2008 field trial results at Wooster, Ohio: Influence of prothioconazole, yeast antagonist OH 182.9, prothioconazole tolerant variants 3C and 4C of OH 182.9, and combinations thereof on FHB disease parameters on winter wheat cultivar Pioneer Brand 2545[a, b]

| | Wheat Cultivar Pioneer Brand 2545 | | | | | |
|---|---|---|---|---|---|---|
| Treatment[c] | DS (%) | DI (%) | FDK (%) | Yield bu/A | TWT lbs/bu | DON (ppm) |
| Untreated control | $11.9^{A}$ | $32.4^{A}$ | $42.5^{A}$ | $47.4^{C}$ | $47.3^{D}$ | $8.1^{A}$ |
| Proline (5 oz/acre) | $3.5^{BC}$ | $11.3^{BC}$ | $12.8^{ABC}$ | $57.8^{AB}$ | $51.4^{A-D}$ | $4.0^{AB}$ |
| OH 182.9 WT | $12.6^{A}$ | $28.0^{A}$ | $29.5^{ABC}$ | $49.4^{BC}$ | $49.0^{A-D}$ | $6.8^{AB}$ |
| OH 182.9 variant 3C | $9.4^{A}$ | $24.3^{AB}$ | $25.5^{ABC}$ | $49.8^{ABC}$ | $47.7^{CD}$ | $6.7^{AB}$ |
| OH 182.9 variant 4C | $9.0^{AB}$ | $22.9^{AB}$ | $17.4^{ABC}$ | $50.4^{ABC}$ | $48.2^{BCD}$ | $6.6^{AB}$ |

TABLE 3-continued 2008 field trial results at Wooster, Ohio: Influence of prothioconazole, yeast antagonist OH 182.9, prothioconazole tolerant variants 3C and 4C of OH 182.9, and combinations thereof on FHB disease parameters on winter wheat cultivar Pioneer Brand 2545[a, b]

| | Wheat Cultivar Pioneer Brand 2545 | | | | | |
|---|---|---|---|---|---|---|
| Treatment[c] | DS (%) | DI (%) | FDK (%) | Yield bu/A | TWT lbs/bu | DON (ppm) |
| OH 182.9 3C + Proline | $2.5^{C}$ | $8.2^{BC}$ | $6.3^{BC}$ | $55.3^{ABC}$ | $52.4^{AB}$ | $4.2^{AB}$ |
| OH 182.9 4C + Proline | $2.8^{C}$ | $8.2^{BC}$ | $12.5^{BC}$ | $58.5^{A}$ | $52.6^{A}$ | $3.5^{B}$ |
| Proline + WT (24 h delay) | $2.6^{C}$ | $8.2^{BC}$ | $15.7^{ABC}$ | $55.6^{ABC}$ | $52.6^{A}$ | $3.9^{AB}$ |
| Proline + 3C (24 h delay) | $2.3^{C}$ | $8.4^{BC}$ | $2.5^{C}$ | $57.1^{AB}$ | $52.2^{AB}$ | $3.5^{B}$ |
| P value | 0.001 | 0.001 | 0.001 | 0.001 | 0.001 | 0.001 |

[a]Within a column, means followed not followed by the same letter are significantly different (P < 0.05 Bonferroni mean separation)
[b]DS = Disease severity, DI = Disease incidence, FDK = *Fusarium* damaged kernels, Yield = Expressed in bushels per acre, TWT = Test weight expressed in pounds per bushel, DON = Deoxynivalenol
[c]Proline = Commercial formulation of prothioconazole applied at a rate equivalent to 5 oz/acre, OH 182.9 WT = Wild type strain of OH 182.9

We claim:

1. A substantially biologically pure microorganism which is a strain of *Cryptococcus flavescens* tolerant to prothioconazole selected from the group consisting of *Cryptococcus flavescens* 3C which has been deposited under deposit accession no. NRRL Y-50378, and *Cryptococcus flavescens* 4C which has been deposited under deposit accession no. NRRL Y-50379.

2. The microorganism of claim 1 wherein said strain is said *Cryptococcus flavescens* 3C which has been deposited under deposit accession no. NRRL Y-50378.

3. The microorganism of claim 1 wherein said strain is said *Cryptococcus flavescens* 4C (NRRL which has been deposited under deposit accession no. NRRL Y-50379.

4. A method for suppressing Fusarium head blight in a cereal plant comprising applying to a head of said plant at least a microbial antagonist selected from the group consisting of *Cryptococcus flavescens* 3C which has been deposited under deposit accession no. NRRL Y-50378, and *Cryptococcus flavescens* 4C which has been deposited under deposit accession no. NRRL Y-50379, and combinations thereof, said microbial antagonist being applied in an amount effective to reduce the level of Fusarium head blight relative to that in the corresponding untreated control.

5. The method of claim 4 wherein said microbial antagonist is substantially biologically pure.

6. The method of claim 4 wherein said microbial antagonist is said *Cryptococcus flavescens* 3C which has been deposited under deposit accession no. NRRL Y-50378.

7. The method of claim 4 wherein said microbial antagonist is said *Cryptococcus flavescens* 4C which has been deposited under deposit accession no. NRRL Y-50379.

8. The method of claim 4 wherein said microbial antagonist is applied to the head prior to hard dough stage of development.

9. The method of claim 4 wherein said microbial antagonist is applied to the head during flowering.

10. The method of claim 4 wherein said microbial antagonist is applied to the head prior to flowering.

11. The method of claim 4 wherein said cereal is wheat or barley.

12. The method of claim 8 wherein said cereal is wheat.

13. A composition for suppressing *Fusarium* head blight in a cereal plant comprising a microbial antagonist selected from the group consisting of *Cryptococcus flavescens* strain 3C which has been deposited under deposit accession no. NRRL Y-50378, and *Cryptococcus flavescens* strain 4C which has been deposited under deposit accession no. NRRL Y-50379, and combinations thereof, in an agronomically acceptable carrier.

14. The composition of claim 13 which is substantially biologically pure.

15. The composition of claim 13 wherein said microbial antagonist is said *Cryptococcus flavescens* 3C which has been deposited under deposit accession no. NRRL Y-50378.

16. The composition of claim 13 wherein said microbial antagonist is said *Cryptococcus flavescens* 4C which has been deposited under deposit accession no. NRRL Y-50379.

17. The microorganism of claim 1 which is isolated.

* * * * *